United States Patent
Grodzins

(10) Patent No.: US 7,787,589 B2
(45) Date of Patent: Aug. 31, 2010

(54) IN VIVO MEASUREMENT OF TRACE ELEMENTS IN BONE BY X-RAY FLUORESCENCE

(75) Inventor: Lee Grodzins, Lexington, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 12 days.

(21) Appl. No.: 12/433,569

(22) Filed: Apr. 30, 2009

(65) Prior Publication Data

US 2009/0274268 A1 Nov. 5, 2009

Related U.S. Application Data

(60) Provisional application No. 61/049,373, filed on Apr. 30, 2008.

(51) Int. Cl.
*G01N 23/223* (2006.01)
(52) U.S. Cl. .......................... 378/45; 378/88
(58) Field of Classification Search .................. 378/44, 378/45, 46, 49, 86, 87, 88, 89
See application file for complete search history.

(56) References Cited

U.S. PATENT DOCUMENTS

| | | | |
|---|---|---|---|
| 4,845,729 A | 7/1989 | Rosen et al. | |
| 5,461,654 A | 10/1995 | Grodzins et al. | |
| 7,386,337 B2 | 6/2008 | Puzas | |
| 2004/0022355 A1* | 2/2004 | Kaiser et al. | 378/49 |
| 2004/0125913 A1* | 7/2004 | Larson et al. | 378/50 |
| 2006/0291619 A1* | 12/2006 | Statham | 378/45 |
| 2007/0258561 A1* | 11/2007 | Chikawa | 378/45 |
| 2009/0067572 A1 | 3/2009 | Grodzins et al. | |
| 2009/0262889 A1* | 10/2009 | Dugas et al. | 378/45 |

OTHER PUBLICATIONS

D. R. Chettle et al., "Measurements of Trace Elements In Vivo," Advances In In Vivo Body Composition Studies, Plenum Press (New York), pp. 247-257, (1990).

John F. Rosen et al., "Sequential Measurements of Bone Lead Content by L X-Ray Fluorescence In CaNa2 EDTA-Treated Lead-Toxic Children," Environmental Health Perspectives, pp. 271-277, (1991).

(Continued)

*Primary Examiner*—Hoon Song
(74) *Attorney, Agent, or Firm*—Charles B. Katz

(57) ABSTRACT

Methods for in vivo measurement of lead or other trace elements in bone by x-ray fluorescence (XRF) without independent measurement of underlying tissue thickness are disclosed. In one method, the lead concentration is calculated based on the intensity of a first characteristic fluoresced peak and a function having as an argument the intensity ratio of first and second characteristic fluoresced peaks, with at least one parameter of the function being empirically determined by measurements of calibration phantoms having differing thicknesses of tissue surrogate material. In another method, the lead concentration is measured by estimating tissue thickness based on the intensity of the Compton scattering peak, or ratio of Compton/Rayleigh intensities, and the intensity of a characteristic fluoresced x-ray peak corrected for attenuation by tissue of the estimated thickness. Also disclosed is a method for determining the calcium concentration and density of bone based on XRF spectrum data.

15 Claims, 8 Drawing Sheets

OTHER PUBLICATIONS

Andrew C. Todd et al., "In Vivo X-Ray Fluorescence Of Lead In Bone," Environmental Research, pp. 326-335, (1992).

Philip J. Sandrigan et al., "Direct Measurement Of Lead In Bone—A Promising Biomarker," Editorials, Journal of American Medical Association, vol. 27 (No. 3), pp. 239-240, (1994).

Andrew C. Todd et al., "In Vivo X-Ray Fluorescence Of Lead In Bone: Review And Current Issues," Environmental Health Perspectives, vol. 102 (No. 2), pp. 172-177, (1994).

Howard Hu et al., "Bone Lead Measured by X-Ray Fluorescence: Epidemiologic Methods," Environmental Health Perspectives 103, Supplement 1, Feb. 1995, 13 pages.

Andrew C. Todd et al., "Unraveling The Chronic Toxicity Of Lead: An Essential Priority For Environmental Health," Environmental Health Perspectives, vol. 104, Supplement 1, Mar. 1996, pp. 141-146.

Andrew C. Todd, "L-Shell X-Ray Fluorescence Measurements Of Lead In Bone: Theoretical Considerations," Physics in Medicine and Biology, vol. 47, pp. 491-505, (2002).

Andrew C. Todd, "L-Shell X-Ray Fluorescence Measurements Of Lead In Bone: System Development," Physics in Medicine and Biology, vol. 47, pp. 507-522, (2002).

Andrew C. Todd et al., "L-Shell X-Ray Fluorescence Measurements Of Lead In Bone: Accuracy and Precision," Physics in Medicine and Biology, vol. 47, pp. 1399-1419, (2002).

* cited by examiner

IN VIVO MEASUREMENT OF TRACE ELEMENTS IN BONE BY X-RAY FLUORESCENCE

CROSS-REFERENCE TO RELATED APPLICATION

This application claims the priority benefit under 35 U.S.C. §119(e)(1) of U.S. Provisional Patent Application No. 61/049,373 by Grodzins entitled "In Vivo Measurement of Heavy Elements in Bone", filed Apr. 30, 2008, the disclosure of which is herein incorporated by reference.

FIELD OF THE INVENTION

The present invention relates generally to methods and apparatuses for in vivo measurement of the concentration in bone of trace elements, such as lead, and more particularly to in vivo measurement of the concentration in bone of trace elements utilizing x-ray fluorescence.

BACKGROUND OF THE INVENTION

Lead toxicity is a serious environmental and societal problem affecting intelligence, behavior and health. Lead toxicity is defined by the U.S. Center for Disease Control in terms of the lead concentration in blood: a lead content in blood above 25 micrograms per deciliter of whole blood, associated with an erythrocyte proptoporphyrin concentration of at least 35 micrograms per deciliter, is considered toxic. A test for lead in blood, however, reflects only the exposure during the few months prior to the test and may not reflect the whole-body burden. Accordingly, when the blood test indicates lead poisoning, a further test is performed before treatment to determine the skeletal lead burden. These time-consuming and burdensome tests require the analysis of the urine following the administering of a chelating agent that causes lead to be removed from fluids and bone.

An alternative diagnostic approach involves measuring the skeletal lead concentration in vivo by x-ray fluorescence (XRF). XRF-based in vivo analysis for lead began in the mid-1970's with the pioneering work at the University of Lund in Sweden. The development and relative merits of the principal techniques employed for XRF-based skeletal lead measurement are discussed in the review article by Todd and Chettle entitled "In Vivo X-Ray Fluorescence of Lead in Bone: Review and Current Issues" (*Environment Health Perspectives*, vol. 102, no. 2 (February 1994)), the contents of which are incorporated herein by reference. The standard technique adopted by research laboratories throughout the world for the in vivo study of lead in bone uses the 88 keV gamma ray emitted by the radioactive source $Cd^{109}$ to fluoresce the K x-rays of lead. State-of-the-art instruments employing this technique have detection limits of a few parts per million, allowing researchers to explore potential toxicities in wide groups of the population.

While offering excellent sensitivity, accuracy and precision, the standard technique has significant problems associated therewith. Utilization of a radioisotope source has inherent disadvantages: it cannot be turned off, requires licensing and periodic replacement, and poses onerous problems with disposal. Furthermore, testing conducted by the standard K x-ray technique requires about thirty minutes (during which the subject must be immobilized) to gather sufficient counts for statistically significant measures of the lead concentration. That long duration, with its concomitant costs, precludes the test being used for routine clinical evaluations.

The disadvantages of the standard K x-ray technique have prompted exploration of the potential of measuring the lead concentration using the L x-rays of lead, fluoresced responsive to irradiation by relatively low-power x-rays that can be generated by x-ray tubes. The $L_\alpha$ and $L_\beta$ x-rays, at 10.5 keV and 12.6 keV respectively, have little penetrating power so that the measurements are typically restricted to bones, such as the tibia and patella, with minimal overlying tissue, and only the first quarter-millimeter of the bone is investigated. In an early example of this approach disclosed by Rosen et al. in U.S. Pat. No. 4,845,729, screening for lead toxicity is performed by irradiating a test subject's tibia with x-rays produced by a silver-anode x-ray tube, and acquiring a spectrum of the fluoresced radiation and comparing the $L_\alpha$ and $L_\beta$ x-ray peaks to the corresponding peaks in spectra obtained from patients diagnosed (by the conventional blood testing) with lead toxicity.

As is extensively discussed by Todd et al. in "L-Shell X-Ray Fluorescence Measurements of Lead in Bone: Accuracy and Precision" (*Phys. Med Biol.*, vol. 47, pp. 1399-1419 (2002)), a significant limitation on the accuracy and precision of lead concentration measurements based on detection of L x-rays arises from the sensitivity of such measurements on the thickness of tissue overlying the irradiated bone. While various direct and indirect techniques are currently available (e.g., ultrasound gauges) for determination of overlying tissue thickness, such techniques may yield results having relatively large inherent variability, thereby compromising the accuracy and precision of lead concentration measurements that rely on determination of tissue thickness. Moreover, the overlying tissue is not homogeneous but instead consists of both skin and adipose tissue (subcutaneous fat), which attenuate the L x-rays differently, so that both thicknesses must be known in the conventional methods of analysis if the concentrations are to be measured accurately.

In U.S. Pat. No. 5,461,654, the contents of which are incorporated herein by reference, Grodzins et al. propose an XRF-based method for determination of the concentration of lead and bone from the intensities of the $L_\alpha$ and $L_\beta$ x-rays that is purportedly insensitive to the thickness and composition of the tissue overlying the irradiated bone. It is believed by the present inventor, however, that this proposed method, which is based upon a thin-layer approximation of the lead-containing bone, may not produce reliable results for bones of clinical interest, i.e., bone having a thickness in excess of 1 mm and thus being "infinitely" thick for the L x-rays of lead.

SUMMARY

Embodiments of the present invention provide XRF-based methods and apparatuses for in vivo measurement of the concentration in bone of a specified trace element, such as lead, which provide reliable results without requiring independent experimental determination of the thickness of tissue overlying the irradiated bone. In a first embodiment, a portion of a bone with overlying tissue is irradiated with x-rays having energies suitable for causing the specified trace element to fluoresce, producing first and second fluoresced emission peaks characteristic of the trace element (e.g., the $L_\alpha$ and $L_\beta$ x-ray peaks of lead). The concentration of the trace element is then calculated based on the measured intensities of the first emission peak and a function having as an argument the ratio of the intensities of the first and second fluoresced emission peaks, the function having at least one empirically determined parameter and being representative of the attenuation of the overlying tissue thickness.

In a second embodiment, the intensity of one fluoresced emission peak is measured (e.g., the $L_\beta$ x-ray peak of lead), along with the intensity of a Compton scattering peak resulting from the inelastic scattering of radiation producing the fluoresced emission peak. The thickness of overlying tissue is estimated based on an empirically predetermined relationship between tissue thickness and the Compton scattering peak intensity, and the concentration of the trace element is then calculated based on the measured intensity of fluoresced emission peak, corrected for attenuation produced by tissue of the estimated thickness. In a variation of the second embodiment, the tissue thickness is estimated from measured intensities of the Compton and Rayleigh (elastic) scattering peaks and a predetermined relationship between tissue thickness and the ratio of the measured Compton and Rayleigh scattering peak intensities.

The present invention also provides a technique for estimating the calcium concentration and density of the irradiated bone. This information is useful for normalizing the measured trace element concentration to the calcium concentration, and for adjusting the bone factor ratio employed for calculation of trace element concentration. According to this aspect of the invention, the thickness of overlying tissue is estimated based on the ratio of the measured intensities of the Compton and Rayleigh scattering peaks in the experimentally acquired spectrum. The contribution of the irradiated bone to the Compton and Rayleigh scattering peaks is determined by subtracting the expected contribution of the overlying tissue to the Compton and Rayleigh scattering peaks, which is derived from a predetermined relationship between tissue thickness and scattering peak intensities. The calcium concentration and density may then be estimated from the ratio of Compton to Rayleigh scattering intensities in the bone contribution to the spectrum, using empirically established relationships.

DETAILED DESCRIPTION OF EMBODIMENTS

Embodiments of the present invention are described in the context of their use for in vivo measurement of the concentration in bone of a particular trace element, namely lead. However, it should be understood that the techniques described and depicted herein are useful for measurement of a variety of trace elements of interest, including but not limited to strontium, mercury, cadmium and selenium. Thus, unless specifically limited to lead, the claims should be construed as extending to the full range of elements suitable for measurement using the techniques of the invention. It should also be noted that embodiments of the invention are suitable for use in both human and animal test subjects.

Figure 1:
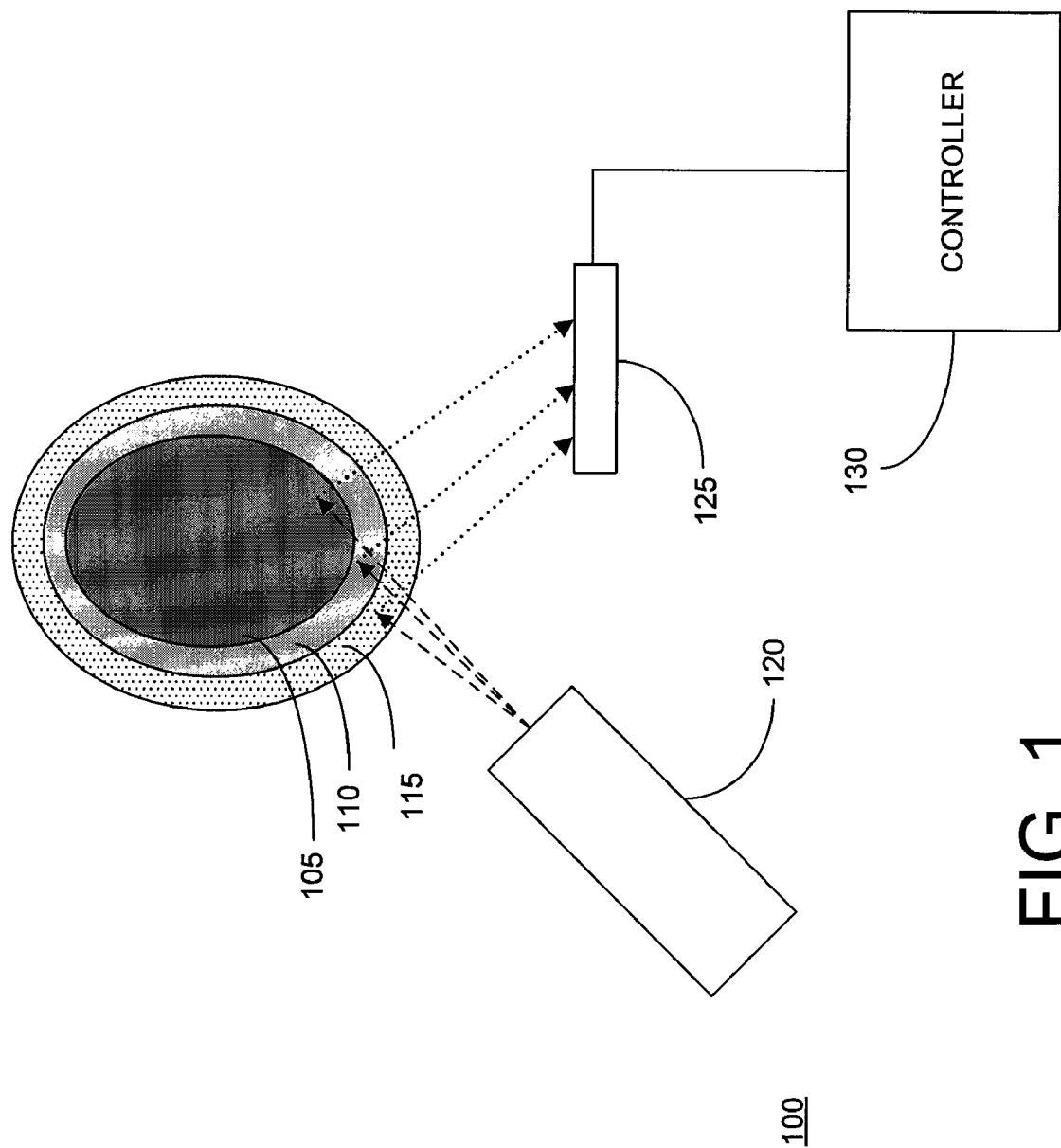
FIG. 1 is a symbolic diagram of an XRF analyzer that may be utilized for the in vivo measurement of the concentration of a specified trace element in bone, in accordance with embodiments of the present invention.

FIG. 1 depicts an XRF analyzer 100 disposed to measure the lead concentration of bone 105 covered by a relatively thin layer of tissue (typically <~5 mm in thickness) consisting of adipose tissue 110 (subcutaneous fat) and skin 115 (typically ~1 mm in thickness). In human test subjects, it is generally preferable to select the tibia, patella, or other bone with minimal overlying tissue thickness for measurement. Since measurements may be sensitive to any changes in the relative positioning of XRF analyzer 100 and bone 105, a brace or other structure (not depicted, but well known in the art) may be employed to hold the irradiated portion of the test subject immobile during the measurement process. XRF analyzer 100 includes an x-ray source 120 for generating a beam of x-rays to irradiate the selected portion of bone 105. X-ray source 120 may include a device, such as an x-ray tube, for producing x-rays, as well as any suitable structures or devices known in the art for energetically and/or geometrically tailoring the x-ray beam for the XRF measurement; for example, x-ray source 120 may include one or more filters positioned in the beam path to create a substantially monoenergetic x-ray beam, and a collimator for shaping the beam cross-section to appropriate dimensions. As used herein, the term "x-ray" is broadly defined to include any radiation having an energy suitable for causing fluorescence of the trace element of interest via ejection of an inner shell electron, and may encompass radiation classified as gamma-rays in other contexts. In one specific implementation, x-ray source 120 includes an x-ray tube having a silver anode, which produces x-rays at energies of 22 keV and 25 keV, and a silver filter for removing or substantially attenuating x-rays at other energies in order to produce a substantially monoenergetic beam. Generally, the selection of the anode and filter materials will be guided by an objective of producing an x-ray beam having an energy that excites lead or other trace element of interest, and which does not produce scattered radiation at energies that interfere with the characteristic energies of the x-rays fluoresced by the specified trace element.

As shown in FIG. 1, the x-ray beam emitted from x-ray source 120 (referred to herein as the "fluorescing beam" or "exciting beam") irradiates a portion of bone 105 and overlying layers of adipose tissue 110 and skin 115. Some of the x-rays in the fluorescing beam are absorbed or back-scattered by adipose tissue 110 and skin 115. The remaining x-rays enter bone 105 and are either absorbed, thereby producing fluoresced x-rays having energies characteristic of the absorbing elements, or are scattered. The characteristic fluoresced x-rays of the major components of the bone, including calcium and phosphorous, have insufficient energy to penetrate the overlying adipose tissue 110 and skin 115 layers and are therefore not detectable. In contrast, fluoresced x-rays from relatively high-Z trace elements such as lead and strontium have energies sufficient to penetrate the overlying tissue layers and are emitted from the surface of skin 115.

Detector 125 is positioned to receive radiation produced by the interaction of the fluorescing x-ray beam with the irradiated portion of bone 105 and overlying tissue layers. As will be discussed in further detail below, the radiation received by detector 125 (hereinafter referred to as the "detected radiation" or "emitted radiation") will consist of a mixture of elastically scattered (Rayleigh) and inelastically scattered (Compton) radiation from tissue 110, skin 115 and bone 105, and fluoresced x-rays from trace elements in bone 105. The design and operation of detectors for XRF analysis are well-known in the art and hence need not be discussed in detail herein. In various implementations, detector 125 may take the form of a silicon PIN detector, cadmium telluride detector, or silicon drift detector. Detector 125 generates a signal representative of the numbers and energies of x-ray photons incident thereon. This signal is conveyed to a controller 130, which may include a microprocessor that executes program instructions stored in an associated memory for construction of spectra and manipulation and output of data. Controller 130 may be further programmed to regulate the operation of other components of XRF analyzer 100, such as the application of power to the x-ray tube and the selection of filtering materials.

X-ray source 120, detector 125 and controller 130 may be located within a common housing designed to be handheld by the operator, or held in a fixture. A touch screen display (not depicted) may be incorporated into the housing to present text and graphics and to accept operator input. In alternative implementations, certain of the components of XRF analyzer may be located remotely from each other, e.g., components of controller 130 may reside on a general purpose computer that communicates with x-ray source 120 and controller 130 over a wired or wireless connection.

Figure 2:
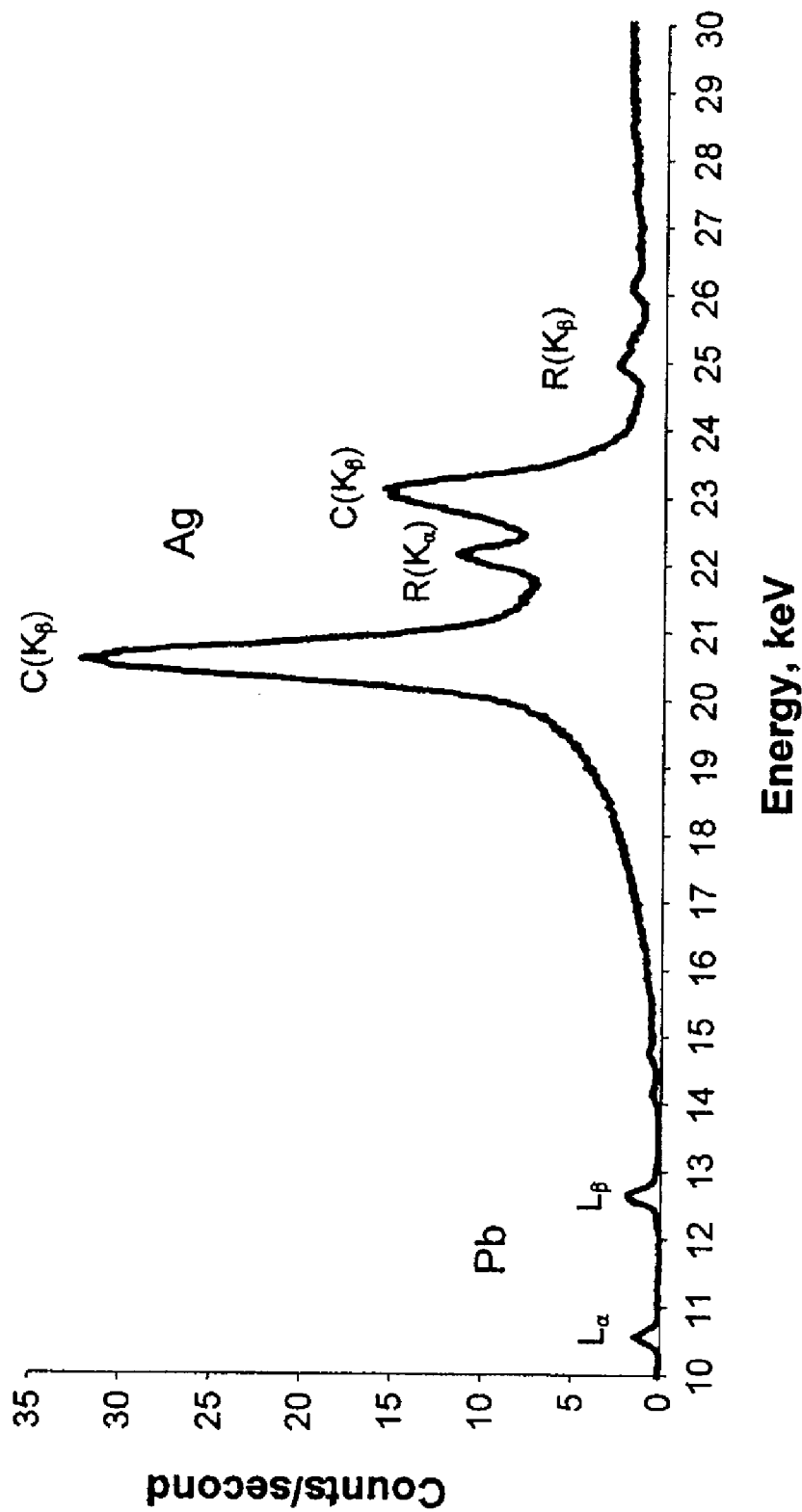
FIG. 2 is an example of a spectrum of detected radiation from a bone with overlying tissue, showing in particular the $L_\alpha$ and $L_\beta$ x-ray peaks of lead and the peaks produced by Compton and Rayleigh scattering of the fluorescing x-ray beam.

FIG. 2 is an example of the spectrum of detected radiation produced by a bone phantom containing 802 ppm of lead in response to irradiation with silver K x-rays at 22 and 25 keV, showing in particular peaks corresponding to the characteristic L x-rays of lead and Compton and Rayleigh scattering of the x-rays in the fluorescing beam. The bone phantom is composed of a lead-doped bone-surrogate material (PVC) covered by a layer of polymethyl methacrylate (PMMA, sold under the trade names Lucite and Plexiglas), which is a surrogate for adipose tissue and skin. The spectrum of the detected radiation is dominated by Compton ($C(K_\alpha)$ and $C(K_\beta)$) and Rayleigh ($R(K_\alpha)$ and $R(K_\beta)$) scattered radiations, with relatively small peaks appearing at the energies of the $L_\alpha$ and $L_\beta$ x-rays of lead.

The basic equations for the intensities (I) of detected radiation attributable to bone, adipose tissue and skin are presented in Equations 1 to 4. The equations ignore terms that are nonessential to the practice of the present method, i.e., the spectral distribution of the exciting and detected radiations, detector efficiencies, and geometrical factors such as the angles the incident and fluoresced radiations make with the normal to the sample surface, and the finite distance between the sample and detector. These factors depend on the specifics of the XRF instrument used for spectrum acquisition and are typically determined empirically as a function of energy using standards of known composition.

The parameters $\mu$, $\rho$ and t are the mass absorption coefficients, densities and thicknesses of the materials respectively. The superscripts S, A, and B designate the skin, adipose and bone. The subscripts, C, R, PE, and L designate the partial interactions leading to Compton, Rayleigh and photoelectric L radiations respectively. The subscripts "in" and "out" refer to the total interactions of the fluorescing radiations into the sample and the fluoresced radiations out from the sample. The $\mu$ values depend on both the materials and the energy of the x-rays traversing the materials. Table I, appearing below, lists values of $\mu$ corresponding to the $L_\alpha$ and $L_\beta$ x-ray peaks of lead and the $K_\alpha$ and $K_\beta$ x-ray peaks of strontium for skin, adipose tissue, and a variety of surrogate materials.

TABLE I

| Material | $\mu_{L\alpha}$ Pb | $\mu_{L\beta}$ Pb | $\mu_{L\alpha}/\mu_{L\beta}$ | $\mu_{K\alpha}$ Sr | $\mu_{K\beta}$ Sr | $\mu_{K\alpha}/\mu_{K\beta}$ | $\mu$ 22 keV |
|---|---|---|---|---|---|---|---|
| Skin | 3.68 | 2.14 | 1.72 | 1.55 | 1.13 | 1.37 | 0.508 |
| Adipose Tissue | 2.43 | 1.44 | 1.69 | 1.06 | 0.79 | 1.34 | 0.323 |
| Lucite | 2.74 | 1.61 | 1.69 | 1.18 | 0.87 | 1.36 | 0.415 |
| Poly-ethylene | 1.69 | 1.02 | 1.66 | .77 | .587 | 1.31 | 0.326 |
| Bone Cortical | 23.3 | 13.8 | 1.69 | 10 | 7.2 | 1.39 | 2.79 |
| PVC37 | 19.0 | 11.2 | 1.70 | 8.1 | 5.8 | 1.40 | 2.25 |

A. Skin: The outer layer is composed primarily of oxygen together with hydrogen and carbon. The only detectable radiations from these elements are Compton and Rayleigh scattering.

$$I_{C,R}^S = I_O \frac{\mu_{C,R}^S}{\mu_{in}^S + \mu_{out}^S}\left[1 - e^{-(\mu_{in}^S + \mu_{out}^S)\rho^S t^S}\right] \qquad (1)$$

B. Adipose tissue: The fluoresced spectrum from the adipose tissue, with a density of 0.9 g/cc, also consists primarily of Compton scattered radiation, with no detected characteristic x-rays. The intensity of the fluoresced radiation from this layer must account for the absorption of the incident and fluoresced radiation through the skin layer. The mass absorption coefficients, $\mu$ for adipose and skin are almost the same; see Table I.

$$I_C^A = I_O \frac{\mu_C^A}{\mu_{in}^A + \mu_{out}^A}\left[1 - e^{-(\mu_{in}^A + \mu_{out}^A)\rho^A t^A}\right] e^{-(\mu_{in}^S + \mu_{out}^S)\rho^S t^S} \qquad (2)$$

The total Compton intensity is the sum of equations (1) and (2).

$$I_C^T = I_O \frac{\mu_C^S}{\mu_{in}^S + \mu_{out}^S}\left[1 - e^{-(\mu_{in}^S + \mu_{out}^S)\rho^S t^S}\right] + \\ \frac{\mu_C^A}{\mu_{in}^A + \mu_{out}^A}\left[1 - e^{-(\mu_{in}^A + \mu_{out}^A)\rho^A t^A}\right] e^{-(\mu_{in}^S + \mu_{out}^S)\rho^S t^S)} \qquad (3)$$

C. Bone: The bone of interest is the cortical bone, with a density of about 1.9 g/cc and with calcium making up about one-fifth of its mass. The 3.7 keV characteristic x-rays of calcium are completely absorbed by the skin and adipose tissue and are not detected by the detector. The $L_\alpha$ and $L_\beta$ x-rays of lead fluoresced in the bone are heavily absorbed by the bone itself. As a consequence, the L x-rays measure the lead in the near-surface of the bone; more precisely in the first 0.3 mm or so of depth. Thus the bone is "infinitely" thick for XRF of the L x-rays of lead.

The XRF intensity of $L_\alpha$ and $L_\beta$ radiations from a lead concentration f in an "infinitely" thick, bare bone, i.e., without a cover of skin and adipose tissue, is:

$$I^B_{L_{\alpha,\beta}} = I_O f \left[ \frac{\mu^{Pb}_{PE,L_{\alpha,\beta}}}{\mu^B_{in} + \mu^B_{L_{\alpha,\beta}}} \right] \quad (4)$$

The factor, $\mu_{PE,L_{\alpha,\beta}}^{Pb}$ is independent of the matrix but does depend on the fluorescing energy. The denominator factors are both energy and material dependent. In particular, both terms increase with calcium concentration. Expected variations in calcium concentrations result in changes of as much as 25% in the bracket term of Equation 4.

Adding the absorption of the incident and fluoresced L x-rays by the adipose tissue and the skin we obtain Equation 5 for the strengths of the $L_\alpha$ and $L_\beta$ lines.

$$I^B_{L_{\alpha,\beta}} = I_O f \left[ \frac{\mu^{Pb}_{PE,L_{\alpha,\beta}}}{\mu^B_{in} + \mu^B_{L_{\alpha,\beta}}} \right] e^{-\left(\mu^A_{in}+\mu^A_{L_{\alpha,\beta}}\right)\rho^A t^A} e^{-\left(\mu^S_{in}+\mu^S_{L_{\alpha,\beta}}\right)\rho^S t^S} \quad (5)$$

The elemental compositions of skin and adipose layers are well documented in the International Commission on Radiological Protection (ICRP). These compositions allow accurate calculations of the mass absorption coefficients using the NIST XCOM database (available at http://physics.nist.gov/PhysRefData/Xcom/Text/XCOM.html), and the probabilities for the interaction of incident x-rays in these layers leading to Compton, Rayleigh and characteristic x-rays.

As discussed in the background section, the conventional method for measurement of lead concentration in bone by detection of L x-rays uses the intensity of either the $L_\alpha$ or $L_\beta$ x-ray peak, together with an independent measure of the thickness of the overlying tissue (acquired, for example, with an ultrasound gauge), to obtain the lead concentration by comparing the experimentally determined quantities with a complete set of calibrations, developed using phantoms, of the intensity of the characteristic peak as a function of lead concentration and thickness of the overlying tissue. Techniques embodied in the present invention remove the need for independent measurement of the overlying tissue thickness and avoid the complexity, cost, and uncertainties associated therewith.

Figure 3:
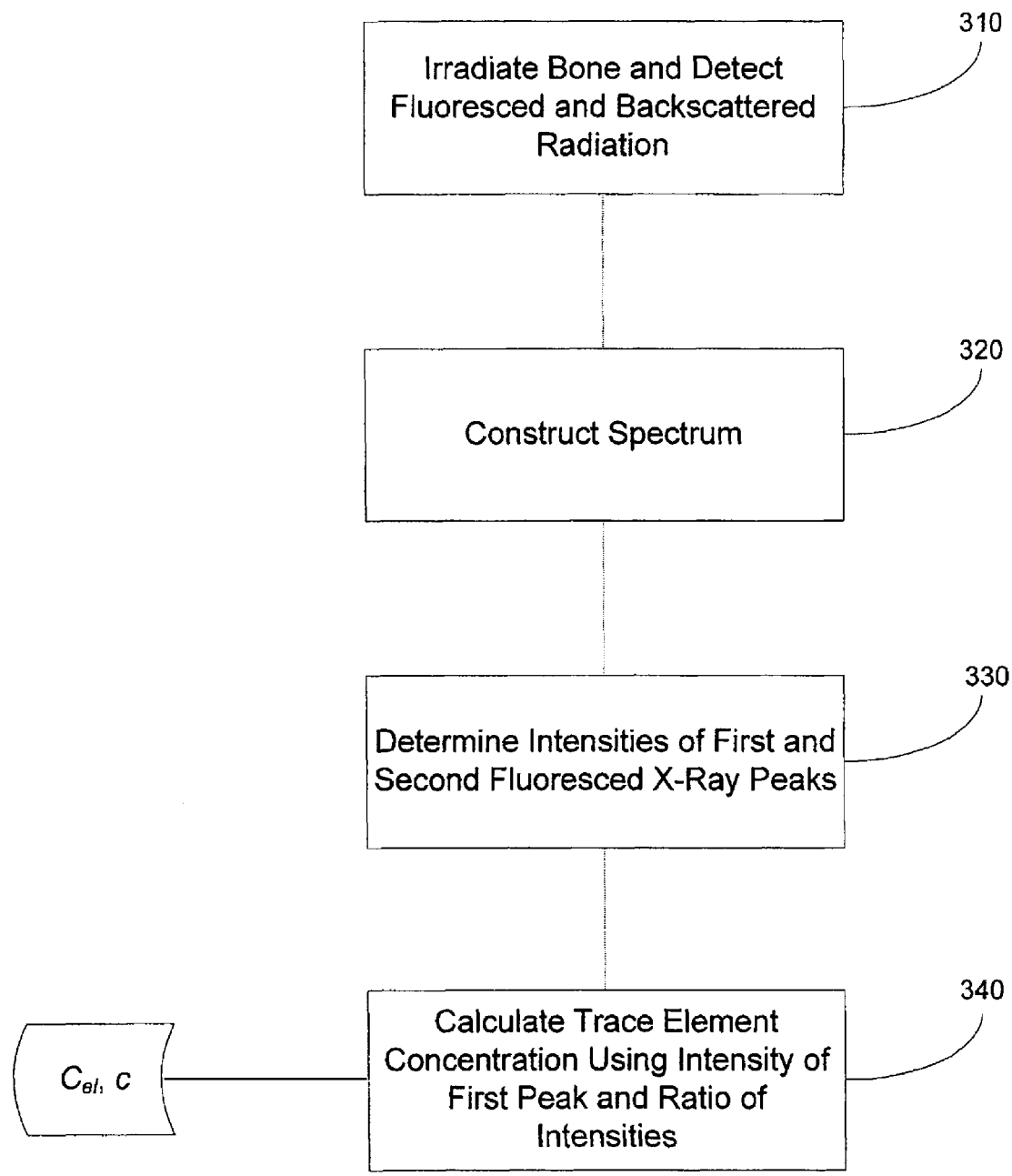
FIG. 3 is a flowchart depicting steps of a method for measuring the concentration of lead in bone according to a first embodiment, wherein the lead concentration is determined from the intensity of one of the two characteristic fluoresced x-ray peaks of lead and a function having as one argument the ratio of intensities of the two characteristic fluoresced x-ray peaks.

FIG. 3 depicts the steps of a method for measuring the concentration of lead (or other specified trace element) in bone using XRF analyzer 100. It should be noted that the ordering of steps in this and other methods described and depicted herein should not be construed as requiring the completion of one step prior to initiating another step. In fact, a preferred implementation of the FIG. 3 method involves performing the irradiation and spectrum acquisition steps 310 and 320 concurrently with the data processing steps 330 and 340, as discussed below. Steps of the method (as well as all other methods described herein) may be encoded as a set of software or firmware instructions executed by controller 130.

In step 310, x-ray source 110 is controlled to direct an x-ray beam onto a selected portion of bone 105 and overlying adipose tissue 110 and skin 115. As discussed above, x-ray beam is composed of radiation having energies suitable for causing atoms of the specified trace element; for example, the K x-rays produced by a silver anode, and/or a silver filter, having energies of 22 and 25 keV, may be used to excite lead. Detector 125 receives radiation from the irradiated portions of bone 105, adipose tissue 110 and skin 115 and generates signals representative of the numbers and energies of x-ray photons incident thereon. These signals are processed by controller 130 to build a spectrum of the detected radiation, step 320. Per FIG. 1 and the accompanying discussion, the spectrum of detected radiation from a lead-containing bone and overlying tissue will include Rayleigh and Compton peaks arising from the coherent and incoherent scattering of x-rays in the exciting beam as well as two characteristic peaks corresponding to the $L_\alpha$ and $L_\beta$ x-rays fluoresced by excited lead atoms (similarly, the spectrum from strontium-containing bone excited by x-rays of suitable energies will contain characteristic peaks corresponding to the $K_\alpha$ and $K_\beta$ x-rays fluoresced by excited strontium atoms.)

In step 330, the intensities of the first and second fluoresced emission peaks characteristic of the trace element (e.g., the $L_\alpha$ and $L_\beta$ x-ray peaks of lead) are determined by integrating or summing the peaks in the spectrum using known algorithms. Processing of the intensity data to determine the lead concentration in bone, as represented by step 340, involves an extension of the thin-layer method described in the aforementioned Grodzins et al. patent. In particular, it extends to bulk lead (or other trace element) the method for measuring the concentration of a thin layer of lead covered by coatings of unknown thickness and composition. Bone that is more than one mm thick is "infinitely" thick for the L x-rays of lead or the K x-rays of strontium. All the bones of clinical interest are therefore "infinitely" thick. One must, therefore include the bracket term in Equation 5. The bracket term is absent if the lead is in a thin layer and was not discussed in the Grodzins et al. patent.

We first consider the method of determining the lead concentration of "standard" bone by measuring only the intensities of the $L_\alpha$ and $L_\beta$ fluoresced x-rays and without knowledge of the thickness of overlying tissue. This measurement is accurate for the normal bone having a density of about 1.9 g/cc and a calcium concentration of about 20%. We consider separately the correction to the measurement when a child is measured or when the calcium concentration of an adult is abnormally low.

The present method does not require knowledge of either the thickness or the composition of the tissues overlying the bone and therefore does not suffer from indefinite knowledge of those tissues. The principal requirement of the new method is the measurement of the intensities of two characteristic x-rays of the analyte: e.g., the 10.5 keV $L_\alpha$ and the 12.6 keV $L_\beta$ for the case of lead in bone, or the 14.1 keV $K_\alpha$ and the 15.8 keV $K_\beta$ for the case of strontium in bone.

The present method makes use of the fact that the photoelectric effect dominates the interaction of the characteristic x-rays interacting with the skin or adipose tissues. When that condition applies, the ratio of the mass absorption coefficients for the $L_\alpha$ and $L_\beta$ lines of lead are independent of the nature of the covering layer. The ratio, given in column 4 of Table 1, is constant to within 1% for materials ranging from polyethylene to bone. Column 7 shows the constancy of the ratio in these materials for the $K_\alpha$ and $K_\beta$ lines of strontium. The method is therefore applicable to both lead and strontium in bone, as well as to other elements that exhibit similar properties.

The constancy of $\mu_\alpha/\mu_\beta$ allows one to solve Equation 5 for the concentration f of lead. The essence of the mathematics is given in the Grodzins et al. patent cited by reference. The bulk lead measurement differs in three respects. First, the concentration of lead is measured in µg per gram of material rather than µg per cm². Second, the intensity of the observed L lines now depends on the absorption coefficients of the bone, which in turn depend on the calcium concentration. Third, the skin and adipose tissues, while of unknown thickness, do not contain any significant amount of an element with atomic number greater than that of oxygen. This fact allows the calcium concentration in the bone to be estimated.

Solving Equation 5 for f making use of the constancy of $\mu_\alpha/\mu_\beta$, we obtain:

$$f = I(L_\beta)\left[\frac{I(L_\beta)}{I(L_\alpha)}\right]^c K, \tag{6}$$

where $I(L_\alpha)$ and $I(L_\beta)$ are the intensities for the two L lines of lead, the exponent c and the constant K are parameters for the particular XRF instrument and are, in the approximations above, $$c = \frac{1}{1 - \mu_a/\mu_b}, \tag{7a}$$

and $$K = \left[\frac{\mu_{in}^B + \mu_\beta^B}{I_0 \mu_{PE}^{Pb}}\right]\left(\frac{\mu_\beta}{\mu_\alpha}\right)^c \tag{7b}$$

The values of c and K are constants determined by using phantoms with known concentrations of lead, as shown below. The bracket term in the denominator of Equation 7b varies with calcium concentration in the bone.

We define a concentration parameter, $C_{Pb}$, which is the normalized f parameter in counts per second per ppm of lead. As will be discussed in further detail below, the $C_{Pb}$ parameter and the exponent c are determined from calibration standards.

$$C_{Pb} = \left\{I(L_\beta)\left[\frac{I(L_\beta)}{I(L_\alpha)}\right]^c K\right\}_{standard} \tag{8}$$

The concentration of lead in an in vivo measurement is then given by the following equation using the measured values of the intensities of the L lines. We emphasize that it is not necessary to know the thickness of the tissues covering the bone.

$$f = \frac{1}{C_{Pb}}\left\{I(L_\beta)\left[\frac{I(L_\beta)}{I(L_\alpha)}\right]^c\right\}_{in\ vivo} \tag{9}$$

Equation 9 can be generalized to trace elements other than lead as follows:

$$f = \frac{1}{C_{el}}\left\{I(F_{1,el})\left[\frac{I(F_{1,el})}{I(F_{2,el})}\right]^c\right\}_{in\ vivo} \tag{10}$$

where $C_{el}$ is the concentration parameter for the specified trace element, and $F_{1,el}$ and $F_{2,el}$ are the first and second characteristic fluoresced x-rays for the specified element.

The concentration parameter $C_{Pb}$ and the exponent c may be empirically determined for a particular XRF analyzer instrument by measurements as a function of the thickness of phantoms of overlying tissues on a phantom of bone with a known concentration of lead. The empirically determined values of $C_{Pb}$ and c may then be stored in the memory of controller 130, and used in step 340 to calculate the lead concentration according to Equation 9. An example of the empirical determination of the concentration parameter $C_{Pb}$ and exponent c for a particular XRF instrument is presented below.

The empirical calibration for $C_{Pb}$ was carried out using a standard of 802 ppm of lead in a special PVC matrix that approximated the bones of mature individuals. It should be emphasized that the determination of the parameter c is independent of the matrix that contains the lead. The only requirement is that the lead concentration is known. The PVC(Pb) standard was covered by successive layers of polymethyl methacrylate, a reasonable surrogate for skin 115 and adipose tissue 110. Data were obtained for thirteen thicknesses, ranging from 0.5 mm to 6 mm. Thirteen values of $C_{Pb}$ were then obtained as a function of the exponent c. The mean value of $C_{Pb}$ and the standard deviation from the mean for the 13 results were then determined for c values ranging from 1.5 to 4. The nominal value of $c=\mu(L_\alpha)/\mu(L_\beta)$ is 1.7 according to the values in Table I; geometrical factors are expected to increase value.

Figure 4:
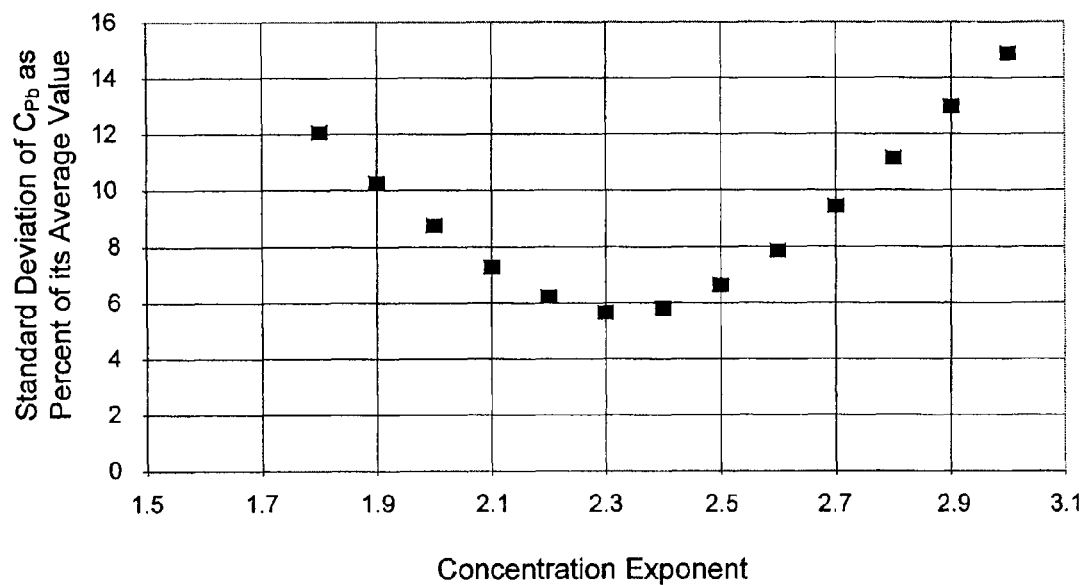
FIG. 4 is a graph depicting the variation of relative uncertainty of the concentration parameter $C_{Pb}$ with the value of the exponent c, the data being derived from measurements performed on bone phantoms having differing thicknesses of tissue-surrogate materials.
Figure 5:
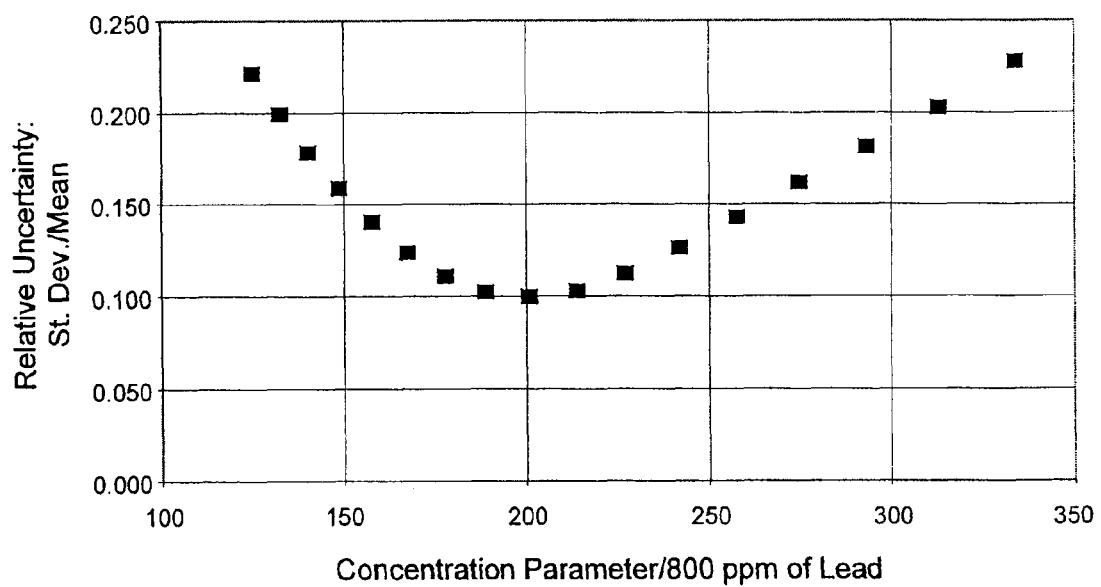
FIG. 5 is a graph depicting the variation of relative uncertainty of the concentration parameter $C_{Pb}$ with the value of $C_{Pb}$.

The results of the calibration analyses are depicted in FIGS. 4 and 5. It may be discerned that values of c and $C_{Pb}$ have clear minima in their relative uncertainties at 2.3 and 200 c/sec per 800 ppm, respectively. These values may be stored and used for the calculation of lead concentration for in vivo testing of test subjects in accordance with step 340 and Equation 9.

Once the concentration of lead in bone 105 has been calculated in step 340, the result may be stored for further analysis and/or displayed or otherwise output to the instrument operator. In certain implementations, the lead concentration may be calculated repeatedly as bone 105 and overlying tissue is irradiated and the resultant spectrum is acquired, and irradiation of the test subject may be terminated when the calculated lead concentration satisfies a specified criterion (e.g., accuracy) in order to minimize the radiation dose to which the test subject is exposed. In other implementations, the lead concentration may be determined from the spectrum utilizing a different method, such as the method described below in connection with FIG. 6, and the results obtained using the two different methods may be compared as a check on reliability. The calculated lead concentration may also be normalized to the concentration of another element, e.g., calcium, as described below in connection with FIG. 8.

Figure 6:
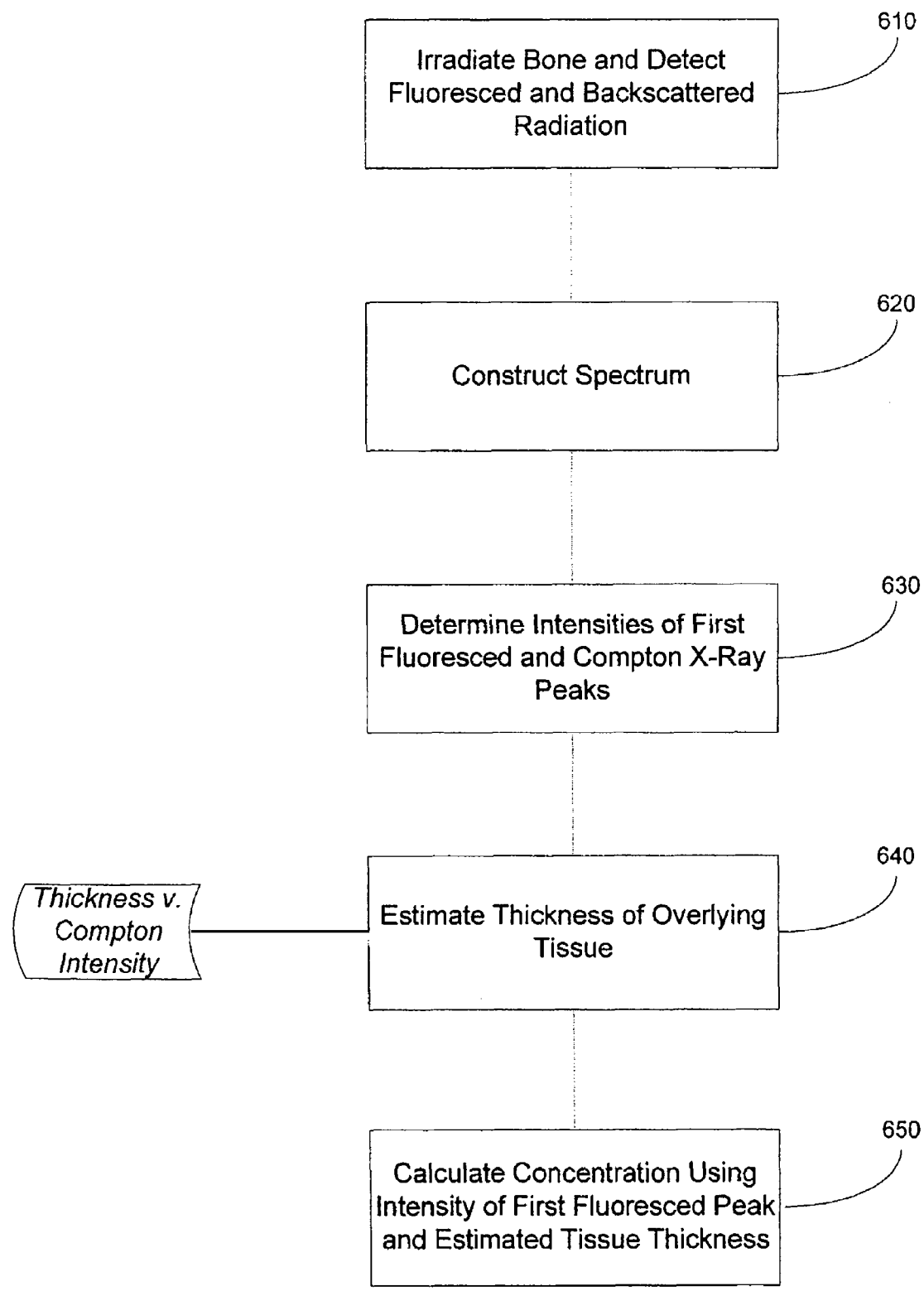
FIG. 6 is a flowchart depicting steps of a method for measuring the concentration of lead in bone according to a second embodiment, wherein the lead concentration is determined from the intensities of the $L_\beta$ x-ray peak of lead and the Compton scattering peak.

FIG. 6 is a flowchart depicting the steps of a method for measuring the concentration of lead or other specified trace element in bone according to a second embodiment of the invention. In contradistinction to the foregoing method, this method does not require detection of two separate fluoresced x-ray peaks, and hence may be utilized when one of the characteristic x-rays fluoresced by the trace element (e.g., the $L_\alpha$ x-ray of lead) is too strongly absorbed by the tissue layers to be reliably measured.

The FIG. 6 method involves irradiating a portion of bone 105 and overlying tissue, step 610, and acquiring the resultant spectrum, step 620, in a manner substantially identical to that described above in connection with FIG. 3. In step 630, the intensity of one of the characteristic fluoresced x-ray peaks of the specified trace element (e.g., the $L_\beta$ x-ray of lead) is determined from the spectrum by conventional integration or summing techniques, along with the intensity of the Compton peak corresponding to inelastic scattering of x-rays in the fluorescing beam (e.g., the Compton peak appearing at an energy of about 20.5 keV in the FIG. 2 spectrum, which is produced by inelastic scattering of the silver $K_\alpha$ x-rays at about 22 keV).

Figure 9:
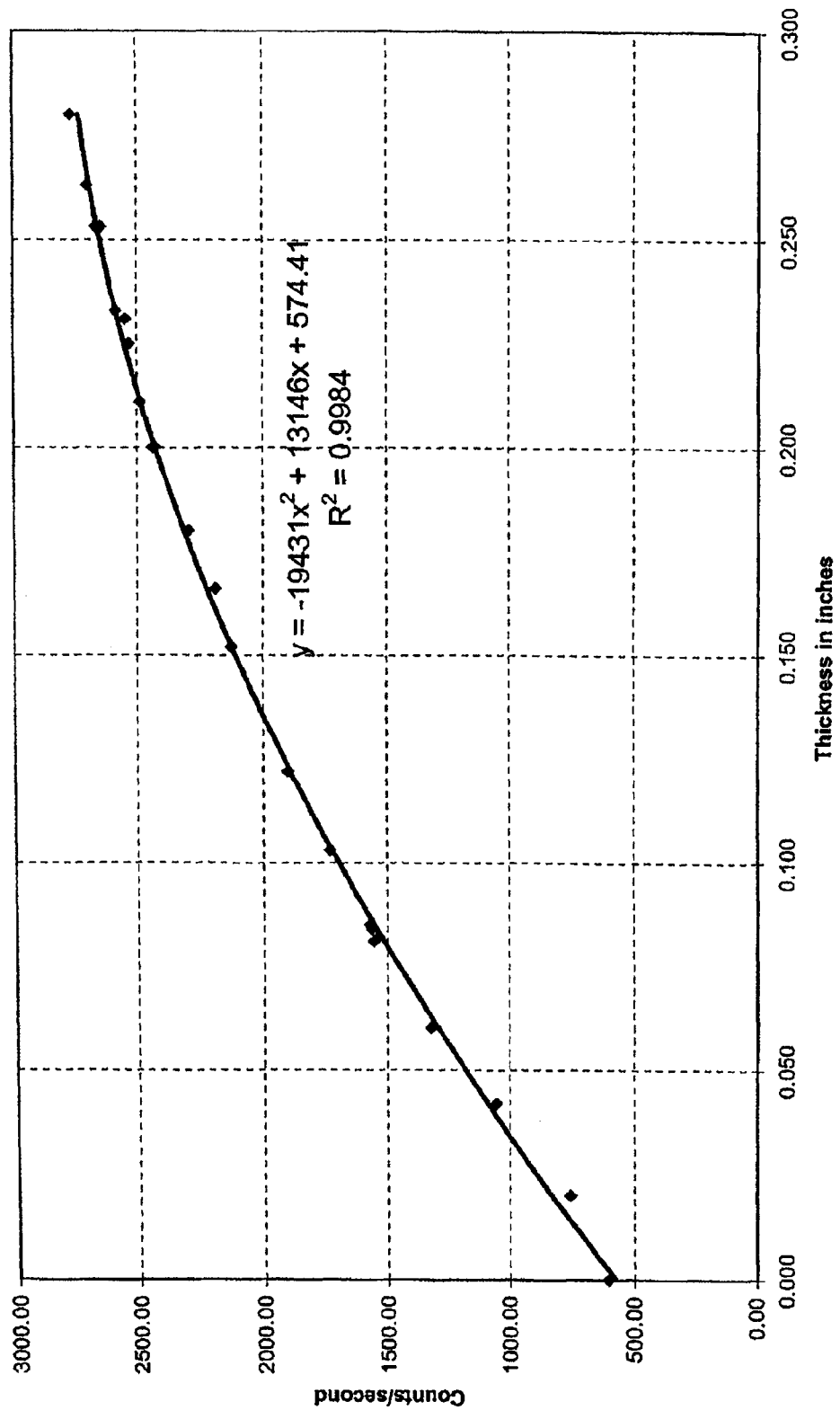
FIG. 9 is a graph depicting an empirically-determined relationship between the Compton scattering peak intensity and thickness of tissue-surrogate material.

Next, the thickness of the tissue overlying the irradiated portion of bone 105, i.e., adipose tissue 110 and skin 115, is estimated based on the measured Compton peak intensity, step 640. This step may utilize an empirically determined relation between Compton peak intensity and overlying tissue thickness obtained for a particular XRF instrument by measurements on bone phantoms with varying thicknesses of a tissue surrogate (e.g., polymethyl methacrylate) overlying the bone surrogate. An illustrative example of an empirically determined relationship between Compton peak intensity and tissue-surrogate thickness is depicted in FIG. 9. The empirically-derived relationship between thickness and Compton peak intensity may then be stored in the memory of controller 130, e.g., in the form of a polynomial function or as a look-up table, and employed during step 640 to estimate tissue thickness based on the Compton peak intensity measured in step 630.

Once the tissue thickness has been estimated, the concentration of lead or other trace element in bone 105 may be calculated from the intensity of the characteristic fluoresced peak in accordance with Equation 5, step 650. The tissue estimate of step 640 is the composite overlying tissue thickness, rather than the separate adipose tissue 110 and skin 115 thicknesses, which is an assumption that may introduce a 20% uncertainty in the result for overlayers that are mainly skin with little adipose. Reasonable assumption of the ratio of skin to adipose will reduce to less than 10% the uncertainty due to this unknown. The calculated result for the concentration of lead or other trace element may be stored and/or displayed or output to the instrument operator. In a manner similar to that described in connection with the FIG. 3 embodiment, the lead concentration may be calculated repeatedly as bone 105 and overlying tissue is irradiated and the resultant spectrum is acquired, and irradiation of the test subject may be terminated when the calculated lead concentration satisfies a specified criterion (e.g., accuracy) in order to minimize the radiation dose to which the test subject is exposed. Also as described, the method of claim 6 may be performed concurrently with other methods (e.g., the FIG. 3 method) to provide a check on results.

In a variation of the FIG. 6 method, the ratio of the intensities of the Compton to Rayleigh peaks may be used to derive an estimate of underlying tissue thickness in place of the Compton peak intensity alone. According to this variation, the intensity of the Rayleigh peak corresponding to elastic scattering of x-rays in the fluorescing beam (e.g., the Rayleigh peak appearing at an energy of about 22 keV in the FIG. 2 spectrum) is determined from the spectrum data in addition to the Compton peak intensity. The estimated tissue thickness is established based on a stored empirically determined relation between the ratio of Compton to Rayleigh peak intensities and overlying tissue thickness. The trace element concentration may then be calculated from the estimated thickness and the measured intensity of the characteristic fluoresced x-ray peak.

Figure 7:
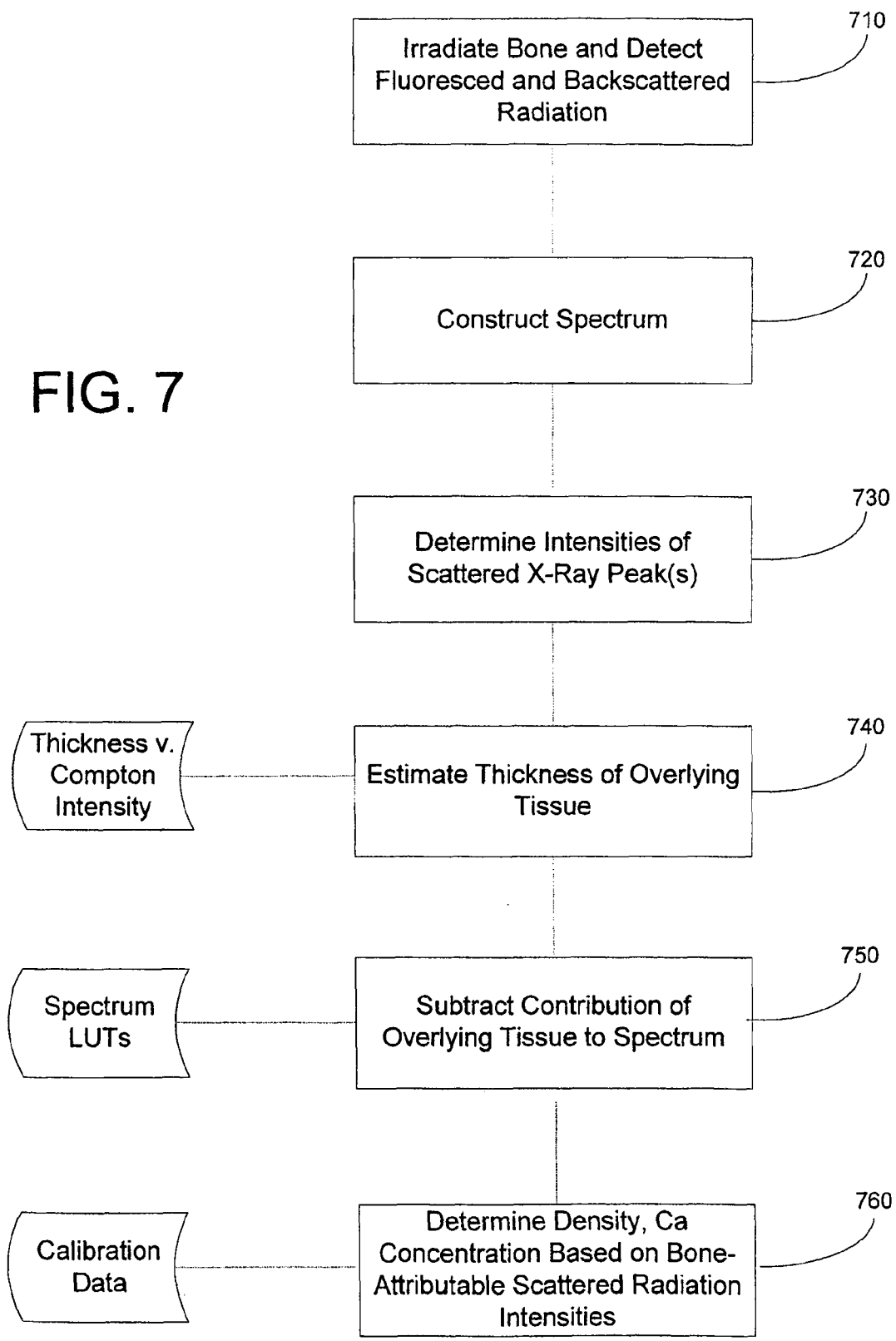
FIG. 7 is a flowchart depicting steps of a method for estimating the calcium concentration and density of the irradiated bone based on a determination of the bone-attributable Compton scattering intensity.

FIG. 7 is a flowchart depicting steps of a method for determining the calcium concentration of bone 105 from data in the acquired spectrum. The calcium concentration in the bone is important information for two independent reasons. First, if the L x-ray measurements are to be compared to those by K x-rays, it is desirable that the lead concentration be stated in micrograms of lead per gram of calcium, because the K x-ray method uses the Rayleigh scattering peak to normalize its K x-ray results, which is equivalent to measuring the lead with respect to the calcium. (The K x-ray methodology, unlike the L x-ray methodology, is substantially indeterminate with respect to the volume or mass of the bone being measured.) Second, the accuracy of measuring the concentration of lead by the L x-ray method depends on the bone factor $$\left[ \frac{\mu_{in}^B + \mu_{L_{\alpha,\beta}}^B}{\mu_{PE,L_{\alpha,\beta}}^{Pb}} \right]$$

in Equation 7b, which in turn depends on the calcium concentration. The ratio of the Compton to Rayleigh intensities for the bone is a direct measure of the calcium concentration—a 50% change in the calcium concentration produces about a 25% change in the bone factor ratio.

The FIG. 7 method involves irradiating a portion of bone 105 and overlying tissue, step 710, and acquiring the resultant spectrum of the detected radiation, step 720, as described above. In step 730, the intensities of the Compton peak corresponding to inelastic scattering of x-rays in the fluorescing beam and of the Rayleigh peak corresponding to elastic scattering of x-rays in the fluorescing beam is determined from the spectrum data.

In step 740, an estimated thickness of the overlying tissue (skin 115 and adipose tissue 110) is determined based on the ratio of the measured Compton to Rayleigh scattering peak intensities. As discussed above in connection with FIG. 6, this step may utilize an empirically determined relation between Compton/Rayleigh peak intensity ratio and overlying tissue thickness obtained for a particular XRF instrument by measurements on bone phantoms with varying thicknesses of a tissue surrogate overlying the bone surrogate. The empirically-derived relationship between thickness and Compton/Rayleigh peak intensity may then be stored in the memory of controller 130, e.g., in the form of a polynomial function or as a look-up table, and employed during step 740 to estimate tissue thickness based on the Compton/Rayleigh peak intensity ratio measured in step 730.

Next, in step 750 the intensities of the Compton and Rayleigh peaks attributable to scattering in bone 105 are determined by subtracting the expected spectrum in the Compton and Rayleigh energy region (about 19-27 keV for excitation by Ag x-rays) for overlying tissue having the estimated thickness from the spectrum from the test subject acquired in step 720. The expected spectrum may be retrieved from a look-up table stored in the memory of controller 130 that encodes a set of calibration spectra obtained using the particular instrument (and at operating parameters equivalent to those under which the test spectrum is acquired) for varying thicknesses of a skin/adipose tissue surrogate (e.g., polymethyl methacrylate). The resulting tissue-subtracted spectrum represents the portions of the detected Compton and Rayleigh scattering peaks produced by scattering in bone 105.

The intensities of the Compton and Rayleigh scattering peaks in the bone-attributable scattering spectrum are then used to estimate the calcium concentration and density of bone 105, step 760. The ratio of Compton to Rayleigh intensities in the bone is essentially independent of geometric factors and is a good measure of the calcium concentration and density of the bone. Estimation of calcium concentration and density of bone 105 may be performed by comparing the ratio of Compton to Rayleigh intensities, as determined in step 750, to the ratio of Compton to Rayleigh intensities expected as a function of density and calcium concentration. This relation may be obtained by empirical calibrations using bone phantoms with known densities and calcium concentrations, or by theoretical calculations.

Figure 8:
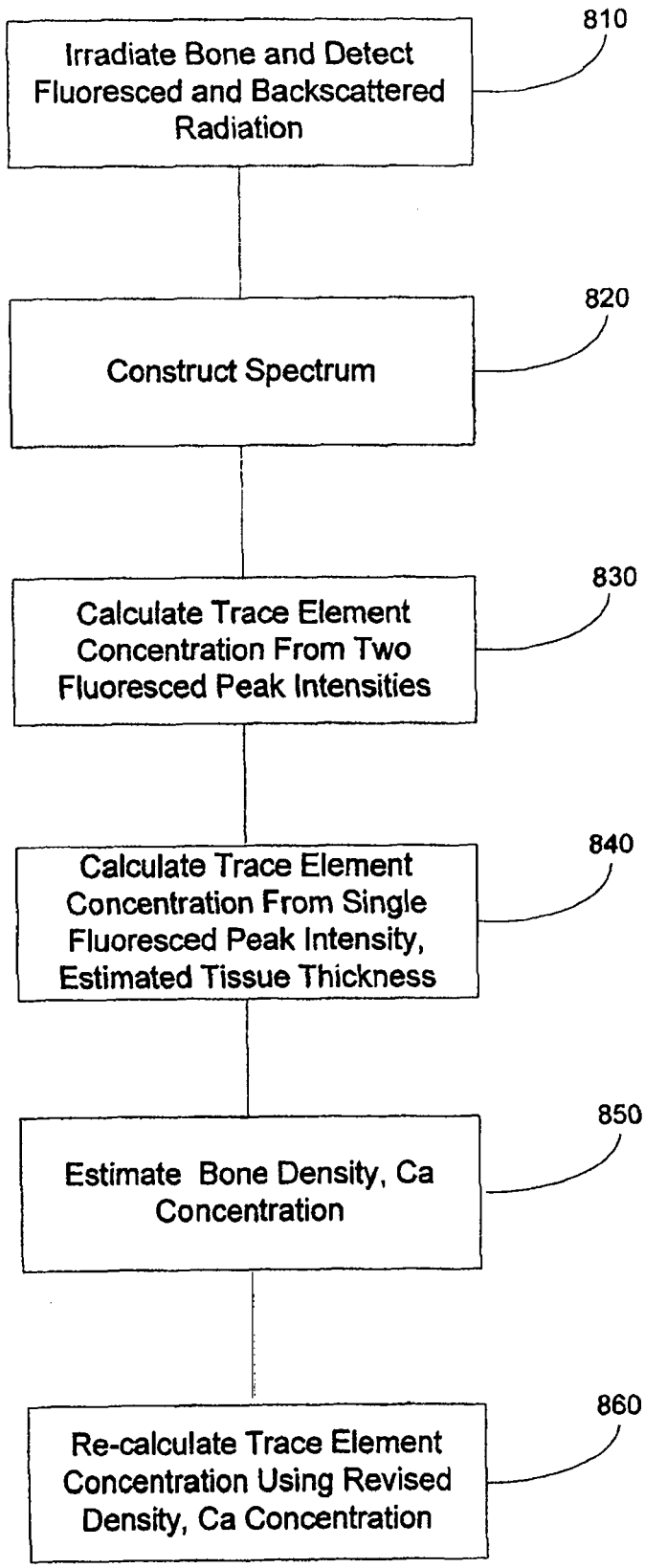
FIG. 8 is a flowchart depicting how the methods represented by FIGS. 3, 6 and 7 may be combined.

As noted above, two or more of the data analysis techniques described above may be performed concurrently in order to provide a check on results, or to allow the measured trace element concentration to be calculated and expressed in a desired form. FIG. 8 illustrates one example of how such concurrent analyses may be conducted. In steps 810 and 820, bone 105 and overlying tissue is irradiated, and a spectrum is obtained of the detected radiation, including both scattered and characteristic fluoresced radiation. The concentration of lead or other specified trace element in bone 105 is determined in step 830 using the method described above in connection with FIG. 3, in which the concentration is calculated based on the intensity of a first fluoresced x-ray peak and a function of the ratio of the intensities of the first and second fluoresced x-ray peaks.

Concurrently with step 830, the concentration of lead or other trace element in bone 105 is determined by the method of FIG. 6, in which an estimate of overlying tissue thickness is obtained based on the Compton peak intensity (or ratio of the Compton/Rayleigh peak intensities), and the concentration is calculated based on the intensity of one fluoresced x-ray peak corrected for the attenuation of the fluoresced x-ray by tissue of the estimated thickness, step 840. As discussed above, this method may produce a more accurate result for lead concentration relative to step 830 when one of the fluoresced x-rays (e.g., the $L_\alpha$ x-ray of lead) is too strongly absorbed to be reliably measured.

In step 850, the calcium concentration and density of bone 105 are estimated in accordance with the FIG. 7 method by identifying the contribution of bone 105 to the Compton and Rayleigh scattering peaks, and comparing the Compton/Rayleigh ratio to calibration data. Again, this step may be performed in parallel with the other analysis steps. In step 860, the lead or other element concentration may be recalculated using a bone ratio parameter (given in Equation 7b) adjusted for the estimated calcium concentration and bone density obtained by step 850, and the lead concentration may be expressed relative to the calcium concentration in units of μg lead/g calcium. In the manner described above, the analyses may be performed repeatedly as the spectrum is acquired, and the measurement may be terminated when the results meet specified criteria.

It is to be understood that while the invention has been described in conjunction with the detailed description thereof, the foregoing description is intended to illustrate and not limit the scope of the invention, which is defined by the scope of the appended claims. Those skilled in the art will recognize that other aspects, advantages, and modifications of and to the described embodiments are within the scope of the following claims.

What is claimed is:

1. A method of in vivo measurement of the concentration of a specified trace element in bone, comprising steps of:
   irradiating a portion of a bone with x-rays having energies suitable for causing the trace element to fluoresce, the irradiated portion of the bone being covered by overlying tissue;
   measuring intensities of first and second fluoresced x-ray peaks characteristic of the trace element; and
   calculating the concentration of the trace element based on the intensity of a selected one of the first and second fluoresced x-ray peaks and a function having as an argument the intensity ratio of the intensities of the first and second fluoresced x-ray peaks, at least one parameter of the function being empirically determined by measurement of samples having different thicknesses of overlying tissue or a surrogate thereof.

2. The method of claim 1, wherein the trace element is lead.

3. The method of claim 1, wherein the trace element is strontium.

4. The method of claim 1, wherein the concentration of the trace element is calculated according to the equation:

$$f = \frac{1}{C_{el}}\left\{I(F_{1,el})\left[\frac{I(F_{1,el})}{I(F_{2,el})}\right]^c\right\}_{in\ vivo}$$

where $C_{el}$ is an empirically determined concentration parameter for the specified trace element, c is an empirically determined exponent, and $F_{1,el}$ and $F_{2,el}$ are the first and second characteristic fluoresced x-rays for the specified element.

5. The method of claim 4, wherein the trace element is lead, and $F_{1,el}$ and $F_{2,el}$ are the $L_\beta$ and $L_\alpha$ x-rays of lead, respectively.

6. The method of claim 1, wherein the step of irradiating the bone comprises using an x-ray tube to generate x-rays.

7. The method of claim 6, wherein the step of irradiating the bone further comprises filtering the x-rays generated by the x-ray tube to produce a substantially monoenergetic beam of x-rays.

8. The method of claim 1, wherein the calculating step is performed concurrently with the irradiating and measuring steps.

9. The method of claim 8, wherein the calculating step is performed repeatedly, and the irradiation step is terminated when the calculated concentration meets a specified criterion.

10. A method of in vivo measurement of the concentration of a specified trace element in bone, comprising steps of:
    irradiating a portion of a bone with x-rays having energies suitable for causing the trace element to fluoresce, the irradiated portion of the bone being covered by tissue;
    measuring intensities of a characteristic fluoresced x-ray peak characteristic of the trace element and a Compton scattering peak resulting from the inelastic scattering of x-rays producing the fluoresced x-ray peak;
    estimating the overlying tissue thickness based on an empirically predetermined relationship between tissue thickness and the Compton scattering peak intensity; and
    calculating the concentration of the trace element based on the estimated tissue thickness and the fluoresced x-ray peak intensity.

11. The method of claim 10, wherein the trace element is lead, and the fluoresced x-ray is the $L_\beta$ peak of lead.

12. The method of claim 10, wherein the trace element is strontium, and the fluoresced x-ray is the $K_\beta$ peak of strontium.

13. The method of claim 10, wherein:
   the irradiating, measuring, estimating and calculating steps are performed concurrently; and
   the calculating step is performed repeatedly, and the irradiation step is terminated when the calculated concentration meets a specified criterion.

14. A method of in vivo measurement of the concentration of a specified trace element in bone, comprising steps of:
   irradiating a portion of a bone with x-rays having energies suitable for causing the trace element to fluoresce, the irradiated portion of the bone being covered by tissue having a thickness;
   measuring an intensity of a fluoresced x-ray peak characteristic of the trace element;
   measuring intensities of a Compton scattering peak and a Rayleigh scattering peak respectively resulting from the inelastic and elastic scattering of x-rays producing the fluoresced emission peak;
   estimating the tissue thickness based on an empirically determined relationship between tissue thickness and the ratio of intensities of the Compton to Rayleigh scattering peak intensities; and
   calculating the concentration of the specified trace element based on the determined tissue thickness and the fluoresced x-ray peak intensity.

15. A method of in vivo measurement of bone calcium concentration/density, comprising steps of:
   irradiating a portion of a bone with x-rays having energies suitable for causing the trace element to fluoresce, the irradiated portion of the bone being covered by tissue;
   measuring intensities of a Compton scattering peak and a Rayleigh scattering peak respectively resulting from the inelastic and elastic scattering of radiation producing the fluoresced emission peak;
   estimating the tissue thickness based on an empirically determined relationship between tissue thickness and the ratio of intensities of the Compton to Rayleigh scattering peak intensities;
   determining the portions of the Compton and Rayleigh scattering peak intensities attributable to bone by subtracting the expected Compton and Rayleigh scattering peak intensities produced by tissue of the estimated thickness; and
   determining the density and calcium concentration of the bone based on the bone-attributable portion of the Compton and Rayleigh scattering peak intensities.

* * * * *